United States Patent [19]
Mannino et al.

[11] Patent Number: 6,048,531
[45] Date of Patent: Apr. 11, 2000

[54] IMMUNOGENIC COMPOSITES CAPABLE OF STIMULATING PRODUCTION OF ANTI-PEPTIDE ANTIBODIES, PHARMACEUTICAL COMPOSITIONS EMPLOYING THESE COMPOSITES AND METHODS OF SELECTIVELY INDUCING PRODUCTION OF ANTI-PEPTIDE ANTIBODIES

[75] Inventors: Raphael James Mannino, Newtonville; Gail Goodman-Snitkoff, Schenectady, both of N.Y.

[73] Assignee: Albany Medical College, Albany, N.Y.

[21] Appl. No.: 08/160,093

[22] Filed: Dec. 1, 1993

Related U.S. Application Data

[63] Continuation of application No. 07/685,986, Apr. 15, 1991, abandoned, which is a continuation of application No. 07/093,660, Sep. 8, 1997, abandoned.

[51] Int. Cl.$^7$ ...................... A61K 39/385; A61K 47/48; C07K 17/06
[52] U.S. Cl. .................... 424/194.1; 424/184.1; 424/283.1; 530/350; 530/403; 530/359
[58] Field of Search .................... 530/402, 403, 530/323, 345, 359, 350; 424/88, 184.1, 193.1, 194.1, 278.1, 283.1; 514/2

[56] References Cited

U.S. PATENT DOCUMENTS

| | | | |
|---|---|---|---|
| 4,396,630 | 8/1983 | Riedl | 424/365 |
| 4,565,696 | 1/1986 | Heath | 424/88 |
| 4,742,048 | 5/1988 | Bouchaudon et al. | 514/17 |
| 4,772,466 | 9/1988 | Allison | 424/88 |
| 4,803,070 | 2/1989 | Cantrell | 424/92 |
| 5,019,383 | 5/1991 | Hopp | 424/88 |

OTHER PUBLICATIONS

W. F. Paul, Fundamental Immunology, 3rd edition, pp. 256–258 and 516–519, 1993.
F. Floc'h, et al. 1981. Ann. Immunol. (Inst. Pasteur) vol. 132 D, pp. 265–270. "Augmentation par des . . . ".
G. Jung, et al. 1985, Angew. Chem. Int. Ed. vol. 24, pp. 872–873. "Increased production of spec . . . ".
J. Metzger, et al. May 29, 1987. Angew. Chem. Int. Ed. pp. 336–338. "Mycoloylpeptides and other lipopeptide . . . ".
W. Prass, et al. Jun. 1987. Biochem et Biophys. Acta, 900:116–128. "Lipopeptides of the N–terminus . . . ".
A Grant Application prepared by Raphael James Mannino, pp. 1–24.
A publication entitled "Practical Immunology" by Leslie Hudson and Frank C. Hay, Blackwell Scientific Publications, pp. 6–11 (Second Edition), 1976, 1980.
Goodman–Snitfoff, et al. "Defining Minimal Requirements for Antibody Production . . . " 8 Vaccine 257 (Jun. 1990).
Gregariadis, "Immunological adjuvants: a role for liposomes" 11:3 Imm. Today 89 (1990).
Goodman–Snitfoff, et al., "Induction of antibody production to synthetic . . . complexes" Tech. Adv. Vaccine Dev. 335 (1988).

*Primary Examiner*—Thomas M. Cuningham
*Attorney, Agent, or Firm*—Sughrue, Mion, Zinn, Macpeak & Seas, PLLC

[57] ABSTRACT

An essentially pure immunogenic composite capable of selectively inducing antibody production in an animal to a peptide that if administered by itself to the animal without being conjugated to or mixed with additional substance does not stimulate production of anti-peptide antibody in the animal. This immunogenic composite comprises: a lipid and an amphipathic peptide. The amphipathic peptide if administered by itself to the animal without being conjugated to or mixed with additional substance does not stimulate production of anti-peptide antibody in the animal. The amphipathic peptide is covalently bound to the lipid in a peptide-lipid complex. The immunogenic composite has a vesicular or an amorphous particulate structure. Another embodiment of this immunogenic composite comprises: a lipid, the amphipathic peptide, and a hydrophilic peptide covalently bound together. The hydrophilic peptide if administered by itself to the animal without being conjugated to or mixed with additional substance does not stimulate production of anti-peptide antibody in the animal.

47 Claims, 5 Drawing Sheets

| NAME | SEQUENCE |
|---|---|
| (NANP)$_3$ | Ac-C-N-A-N-P-N-A-N-P-N-A-N-P-OH |
| h-IL-2(1-12)-Y-TRANS | H-A-P-T-S-S-S-T-K-K-T-Q-L-Y-Q-V-A-V-A-G-L-V-F-L-L-I-S-V-L-L-S-G-L-T |
| HIV(469-485) | H-R-P-G-G-G-D-M-R-D-N-W-R-S-E-L-Y-K-C-NH$_2$ |
| HIV(500-511) | H-K-A-K-R-R-V-U-Q-R-E-K-R-C-NH$_2$ |
| HIV(647-659) | H-E-E-S-Q-N-Q-Q-E-K-N-E-Q-E-C-NH$_2$ |
| HIV(469-511) | H-R-P-G-G-G-D-M-R-D-N-W-R-S-E-L-Y-K-Y-V-K-I-E-P-L-G-V-A-P-T-K-A-K-R-R-V-Q-R-E-K-R-C-NH$_2$ |
| HIV(487-511) | H-K-V-V-K-I-E-P-L-G-V-A-P-T-K-A-K-R-R-V-Q-R-E-K-R-C-NH$_2$ |
| HIV(578-608) | H-A-R-I-L-A-V-E-R-Y-L-K-D-Q-Q-L-L-G-I-W-G-C-S-C-K-L-I-C-T-T-A-V-NH$_2$ |

IMMUNOGENIC COMPOSITES CAPABLE OF STIMULATING PRODUCTION OF ANTI-PEPTIDE ANTIBODIES, PHARMACEUTICAL COMPOSITIONS EMPLOYING THESE COMPOSITES AND METHODS OF SELECTIVELY INDUCING PRODUCTION OF ANTI-PEPTIDE ANTIBODIES

This is a Continuation of application Ser. No. 07/685,986, filed Apr. 15, 1991, now abandonded, which is a Continuation of application Ser. No. 07/093,660, filed Sep. 8, 1987 now abandoned.

FIELD OF THE INVENTION

The present invention is directed to immunogenic composites capable of inducing selective antibody production. In particular, the present invention is directed to immunogenic composites capable of selectively inducing antibody production to both synthetic and naturally occurring peptides without the need to link the peptides to a heterologous protein carrier (e.g. BSA or KLH) and without the need for the peptides to be injected in conjunction with additional adjuvants. The present invention is also directed to a pharmaceutical composition employing the immunogenic composites and to a method for selectively inducing antibody production employing the pharmaceutical composition.

BACKGROUND OF THE INVENTION

The development of effective vaccines is of significant importance in the control and prophalaxis of diseases. The use of synthetic peptides as immunogens is being intensively investigated as one promising approach to the preparation of safe and effective subunit vaccines (Lerner, R. A., Green, N., Alexander, H., Liu, F.-T., Sutcliffe, J. G., and Shinnick, T. M. *Proc. Natl. Acad. Sci. USA* 78:3403–3407 (1981); Bhatnagar, P. K., Papas, E., Blum, H. E., Milich, D. R., Nitecki, D. Karels, M. J., and Vyas, G. N. *Proc. Natl. Acad. Sci. USA* 79:4400–4404 (1982); Neurath, A. R., Kent, S. B. H., and Strick, N. *J. Gen. Virol.* 65:1009–1014 (1984); Dreesman, G. R., Sparrow, J. T., Frenchick, P. J., and Kennedy, R. C. *Adv. Exp. Med. Biol.* 185:129–137 (1985); Thanavala, Y. M., Brown, S. E., Howard, C. R., Roitt, I. M., and Steward, M. W. *J. Exp. Med.* 164:227–236 (1986); Muller, G. M., Shapira, M., and Arnon, R. *Proc. Natl. Acad. Sci. USA* 79:569–573 (1982); Kennedy, R. C., Henkel, R. D., Pauletti, D., Allan, J. S., Lee, T. H., Essex, M. and Dreesman, G. R. *Science* 231:1556–1559 (1986); Bittle, J. L., Houghten, R. A., Alexander, H., Shinnick, T. M., Sutcliffe, J. G., Lerner, R. A., Rowlands, D. J. and Brown, F. *Nature* 298:30–33 (1982) and DiMarchi, R., Brooke, G., Gale, C., Cracknell, V. Doel, T. and Mowat, N. *Science* 232:639–641 (1986)). However, the development of synthetic peptide vaccines has been hampered by the need for both carriers and adjuvants which frequently have undesirable side effects (Lerner, R. A., Green, N., Alexander, H., Liu, F.-T., Sutcliffe, J. G., and Shinnick, T. M. *Proc. Natl. Acad. Sci. USA* 78:3403–3407 (1981); Bhatnagar, P. K., Papas, E., Blum, H. E., Milich, D. R., Nitecki, D. Karels, M. J., and Vyas, G. N. *Proc. Natl. Acad. Sci. USA* 79:4400–4404 (1982); Neurath, A. R., Kent, S. B. H., and Strick, H. *J. Gen. Virol.* 65:1009–1014 (1984); and Muller, G. M., Shapira, M., and Arnon, R. *Proc. Natl. Acad. Sci. USA* 79:569–573 (1982)). In addition, immunization with peptide-protein carrier complexes usually results in the priming of the T cells to the foreign carrier. Hence, a natural infection does not produce a secondary immune response since the animal's T cells are not primed to the natural carrier of the neutralizing epitope.

Accordingly, there still exists a need for effective immunogens which do not require that the peptides be linked to heterologous protein carriers and do not require injection in conjunction with additional adjuvants.

SUMMARY OF THE INVENTION

One object of the present invention is to provide an immunogenic composite and a pharmaceutical composition that simulates the effectiveness of natural infection or vaccination with the currently available procedures (including inactivated or attenuated agents, or macromolecules, or subunits thereof, from the outer surface of infectious agents), without any of the undesirable side effects of the currently available preparations.

A second object of the present invention is to provide an immunogenic composite and a pharmaceutical composition that avoids the problem of priming T cells specific to a heterologous carrier which would not result in a response during subsequent natural exposure.

A third object of the present invention is to provide a method for priming homologous helper T cells which will respond quickly during the natural infection resulting in the secondary immune response.

These and other objects have been achieved by providing an immunogenic composite capable of selectively inducing or enhancing antibody production.

In a first embodiment, the present invention provides an immunogenic composite capable of selectively inducing or enhancing antibody production to a non-immunogenic peptide comprising a peptide-lipid complex which comprises a non-immunogenic amphipathic peptide covalently bound to a lipid. In a preferred embodiment, the peptide-lipid complex is associated with a mixture of one or more lipids and one or more sterols.

In a second embodiment, the present invention provides an immunogenic composite capable of selectively inducing or enhancing antibody production to one or more non-immunogenic peptides comprising a peptide-lipid complex which comprises a hybrid peptide covalently bound to a lipid and said hybrid peptide comprises a non-immunogenic amphipathic peptide covalently bound to one peptide selected from the group consisting of: (a) a non-immunogenic hydrophilic peptide; (b) a non-immunogenic neutral peptide; (c) a non-immunogenic amphipathic peptide; and (d) a hybrid peptide comprising any combination of two or more of the above-defined peptides (a), (b) and (c). In a preferred embodiment the peptide-lipid complex is associated with a mixture of one or more lipids and one or more sterols.

In a third embodiment, the present invention provides an immunogenic composite capable of selectively inducing or enhancing antibody production to one or more non-immunogenic peptides comprising a first peptide-lipid complex and one or more additional peptide-lipid complexes associated with a mixture of one or more lipids and one or more sterols, wherein said first peptide-lipid complex comprises one member selected from the group consisting of: (1) a non-immunogenic amphipathic peptide covalently bound to a lipid; and (2) a hybrid peptide covalently bound to a lipid, wherein said hybrid peptide comprises a non-immunogenic amphipathic peptide covalently bound to a peptide selected from the group consisting of: (a) a non-immunogenic hydrophilic peptide; (b) a non-immunogenic neutral peptide; (c) a non-immunogenic amphipathic peptide; and (d) a hybrid peptide comprising any combination of two or more of the above-defined peptides (2)(a), (2)(b) and (2)(c); and said one or more additional peptide-lipid complexes comprises one or more members selected from the group consisting of: (1) a non-immunogenic hydrophilic peptide covalently bound to a lipid; (2) a non-immunogenic neutral peptide covalently bound to a lipid; (3) a non-immunogenic amphipathic peptide covalently bound to a lipid, and (4) a hybrid peptide covalently bound to a lipid, wherein said hybrid peptide comprises a non-immunogenic amphipathic, hydrophilic or neutral peptide covalently bound to a peptide selected from the group consisting of: (a) a non-immunogenic hydrophilic peptide; (b) a non-immunogenic neutral peptide; (c) a non-immunogenic amphipathic peptide; and (d) a hybrid peptide comprising any combination of two or more of the above-defined peptides (4)(a), (4)(b) and (4)(c).

The present invention also provides a pharmaceutical composition for selectively inducing or enhancing the production of antibodies which comprises a mixture of one or more of the above-described immunogenic composites and a pharmaceutically acceptable carrier, diluent or excipient.

In a further embodiment, the present invention provides a method for selectively inducing or enhancing antibody production comprising administering to a host, in which an immune response is the normal means of defense to infection by foreign materials, a pharmaceutically effective amount of the above-described pharmaceutical composition.

BRIEF DESCRIPTION OF THE DRAWINGS

FIG. 1 shows the primary amino acid sequence of various peptides useful in the immunogenic composites of the present invention.

FIGS. 2, 3, 4 and 5 are profiles derived from Hopp and Woods analysis of peptides useful in the immunogenic composites of the present invention: FIG. 2 shows profiles for amphipathic peptides, HIV(469–511) and HIV(487–511) and for hydrophilic peptides HIV(469–485) and HIV (500–511); FIG. 3 shows a profile for the amphipathic peptide HIV(578–608); FIG. 4 shows a profile for the hydrophilic peptide HIV(647–659); and FIG. 5 shows a profile for the neutral peptide (NANP)$_n$. The asterisks represent the degree of hydrophilicity or hydrophobicity, hydrophilic being above the single letter amino acid code and hydrophobic being below the single letter amino acid code. The greater the number of asterisks, the greater the hydrophilicity/hydrophobicity.

DETAILED DESCRIPTION OF THE INVENTION

Figure 2:
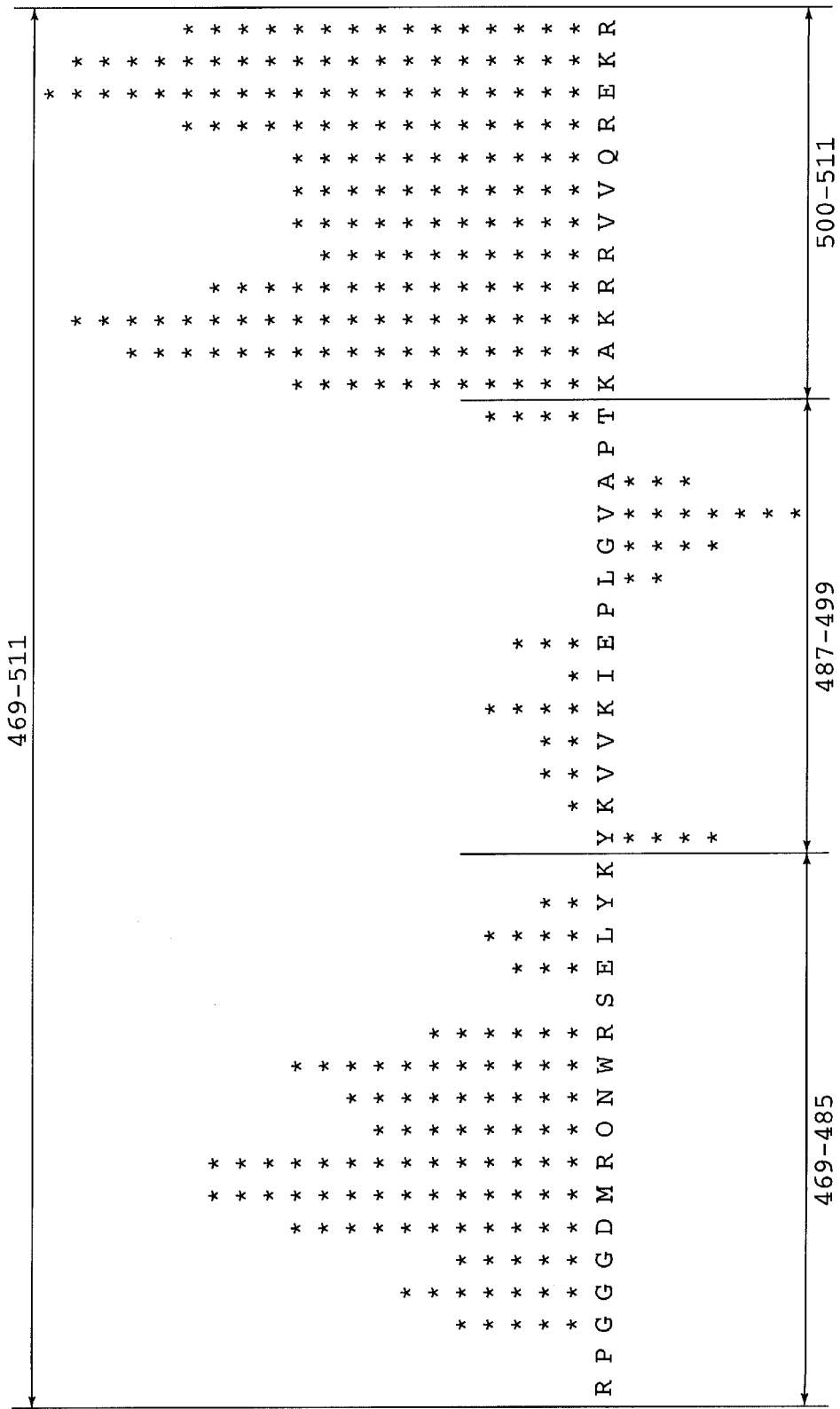

The alphabetical nomenclature used herein for describing peptide sequences is the standard amino acid alphabet set forth below.

| Amino Acid | Three-letter abbreviation | One-letter abbreviation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |

-continued

| Amino Acid | Three-letter abbreviation | One-letter abbreviation |
|---|---|---|
| Glutamine | Gln | Q |
| Glutamic Acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

For purposes of the present invention, the following terms have the definitions set forth below.

Peptide—A series of amino acids polymerized head to tail by a peptide bond between the carboxylic acid group of one and the amino acid group of the next. The peptide can be naturally occurring, recombinantly produced, synthetically produced or derived by chemical or enzymatic cleavage of a large polypeptide or protein so obtained, or by chemical or enzymatic buildup of a peptide from smaller units and the peptide can have moieties other than only amino acids, such as sugars, or can have various chemical modifications such as, for example, phosphorylation, methylation, sulfation or acetylation, these modifications occurring as a result of their production, for example in microorganisms, or by affirmative alteration using organic chemical or enzymatic synthetic techniques.

Non-immunogenic peptide—A peptide, as defined above, but that when administered to an animal without being conjugated to or mixed with additional substances does not stimulate an immune response in that animal. (Some peptides can be immunogenic in one animal but non-immunogenic in an animal of a different allotype. Additionally, as used herein, the term "non-immunogenic peptide" can include peptides that are immunogenic, but whose immunogenicity is enhanced by formation of an "immunogenic composite" according to the present invention.

Amphipathic peptide—A peptide, as defined above, but that contains distinct hydrophobic and hydrophilic regions. Examples of amphipathic peptides are: (1) peptides that contain contiguous stretches of mainly hydrophobic amino acids followed by contiguous stretches of mainly hydrophilic amino acids, or (2) peptides that can assume an alpha-helical structure in solution such that one side of the alpha helix comprises mainly hydrophobic amino acids and the other side of the alpha helix comprises mainly hydrophilic amino acids. The amphipathicity of the second type of peptides is said to have alpha helical periodicity.

The hydrophobic/hydrophilic nature of the regions is defined by computer analysis using programs that take into account the hydrophobic/hydrophilic properties of amino acid side chain residues.

Examples of such programs which can be applied to determine the existence of hydrophobic/hydrophilic stretches are those developed by Hopp and Woods (Hopp T. P. and Woods, K. R. *Proc. Natl. Acad. Sci. USA*

78:3824–3827 (1981) and Hopp T. P. and Woods, K. R. *Mol. Immunol.* 20:483–489 (1983)) or Kyte and Doolittle (Kyte, J. and Doolittle, R. F., *J. Mol. Biol.* 157:105–131 (1982)) although other analogous programs can also be used.

Computer programs have also been developed which can determine the amphipathic nature of a peptide should the peptide form an alpha helical structure in solution. In this instance, a distinct hydrophilic region refers to one side of the alpha helical peptide, while a distinct hydrophobic region refers to the other side of the peptide. An example of such a program is provided by Delisi and Berzofsky, *Proc. Natl. Acad. Sci.* 82:7048 (1985).

Also, for the purposes of this invention, a hydrophobic, hydrophilic or neutral region is defined by computer analysis, either of the primary sequence or with respect to alpha helical periodicity as described above.

One physical test of amphipathicity is the ability to perturb the integrity of a phospholipid membrane. This property can be tested by measuring the ability of the peptide to promote the release of carboxyfluorescein from the internal aqueous space of preformed liposomes as described below. However, not all amphipathic peptides will necessarily perturb the integrity of a phospholipid membrane, and, accordingly, for the purposes of this invention perturbation of a phospholipid membrane is not an absolute requirement of the definition of an amphipathic peptide.

Hydrophobic peptide—A peptide, as defined above, but that is hydrophobic in a Hopp and Woods-type or Kyte and Doolittle-type analysis for contiguous stretches or a Delisi and Berzofsky-type analysis for alpha helical periodicity as described above.

Hydrophilic peptide—A peptide, as defined above, but that is hydrophilic in a Hopp and Woods-type or Kyte and Doolittle-type analysis for contiguous stretches or a Delisi and Berzofsky-type analysis for alpha helical periodicity as described above.

Neutral peptide—A peptide, as defined above, but that is neutral in a Hopp and Woods-type or Kyte and Doolittle-type analysis for contiguous stretches or a Delisi and Berzofsky-type analysis for alpha helical periodicity as described above.

According to the present invention, at least three general embodiments of the immunogenic composite are envisioned.

A first embodiment provides an immunogenic composite capable of selectively inducing or enhancing antibody production to a non-immunogenic amphipathic peptide. The second and third embodiments provide immunogenic composites capable of selectively inducing or enhancing antibody production to a non-immunogenic hydrophilic and/or a non-immunogenic neutral peptide as well as to a non-immunogenic amphipathic peptide.

The composite according to the first embodiment comprises a peptide-lipid complex comprising a non-immunogenic amphipathic peptide covalently bound to a lipid. In a preferred embodiment, the peptide-lipid complex is associated with a mixture of one or more lipids and one or more sterols.

The peptide-lipid complex is prepared by covalently bonding an amphipathic peptide to a suitable lipid according to numerous known means such as, for example, by cross-linking to glycosphingolipids (Heath, T. D., et al. *B.B.A.* 640:66–81 (1981)); or via N-(p-aminophenyl)sterylamide (Snyder, S. L. and Vannier, W. E. *B.B.A.* 772:288–294 (1984)); or via the N-hydroxysuccinimide ester of palmitic acid (Huang, A. et al. *J.B.C.* 255:8015–8018 (1980)).

Covalently binding the peptide to the lipid by cross-linking is preferred and can be accomplished by methods well known in the art, for example, by a method using N-succinimidyl-4-(p-maleimidophenyl)butyrate (Martin, F. J., and Papahadjopoulos, D. *J. Bio. Chem.* 257:286–288 (1982)); N-hydroxysuccinimidyl 3-(2-pyri-dyldithio) propionate (Barbet, J. et al. *J. Supra. Struct. and Cell Biochem.* 16:243–258 (1981)); m-male-imidobenzoyl-N-hydroxysuccinimide ester (Hashimoto, Y. et al. *J. Immuno. Methods* 62:155–162 (1983)); citra-conylation (Jansons, V. K. and Mallett, P. L. *Anal. Biochem.* 111:54–59 (1981)).

As the peptide, any amphipathic peptide that meets the above definition can be used. Of course, if the immunogenic complex is to be used as a vaccine, the peptide should not be toxic or otherwise detrimental to the health of the animal.

Further, as mentioned above, amphipathicity can be tested by measuring the ability of the peptide to promote the release of carboxyfluorescein from the internal aqueous space of preformed liposomes (Szoka and Papahadjopoulos, *Proc. Nat. Acad. Sci. USA* 75:4194–4198 (1978) and Weinstein, J. N. et al., *Science* 195:489–491 (1977)), although this is not a necessary test for purposes of the present invention.

Specifically, carboxyfluorescein (CF) is encapsulated in large unilammelar pospholipid vesicles by known methods (Szoka and Papahadjopoulos, *Proc. Natl. Acad. Sci. USA* 75:4194–4198 (1978)) at self quenching concentrations (~200 mM, Weinstein, J. N. et al., *Science* 195:489–491 (1977)). CF is purified by known methods as described by Ralston, et al (*Biochim. Biophys. Acta.* 649:133–137 (1981)). The ability of peptides to perturb the integrity of the liposomal bilayer can be determined by measuring emission at 520 nm 30 minutes after the addition of peptide to a suspension of liposomes. In general, an increase in fluorescence greater than 5% of the total possible increase is indicative of amphipathicity. Total possible fluorescence increase can be determined by measuring emission at 520 nm before and after lysis of vesicles with 0.1% Triton X-100.

Examples of amphipathic peptides include the following peptides derived from the human immuno deficiency virus, HIV, envelope protein: HIV(487–511), HIV(469–511) and HIV(578–608) (Starcich et al. (*Cell* 45:637–648 (1986)). Further, antibodies to the following sequences recognize the HIV surface glycoprotein or the sequences are included in a region to which neutralizing antibodies are produced: HIV (735–752)(D-R-P-E-G-I-E-E-E-G-G-E-R-D-R-S-NH$_2$, Kennedy et al., *Science* 231:1556–1559 (March 1986)), HIV(340–368)(N-N-T-L-K-Q-I-D-S-K-L-R-E-Q-F-G-N-N-L-Q-S-S-G-C-NH$_2$) alone or HIV(299–329)(H-R-P-N-N-N-T-R-K-I-R-I-E-R-E-P-E-R-A-E-K-I-E-N-M-R-Q-C-NH$_2$) with an amphipathic peptide of HIV (e.g. 487–511) to enhance antibody production. Both HIV(340–368) and HIV (299–329) are from a region of the virus which produces neutralizing antibodies. (Putney et al., *Science* 234:1392–1395 (December 1986)).

The primary sequences of HIV(487–511), HIV(469–511) and HIV(578–608) are set forth in FIG. 1.

Figure 3:
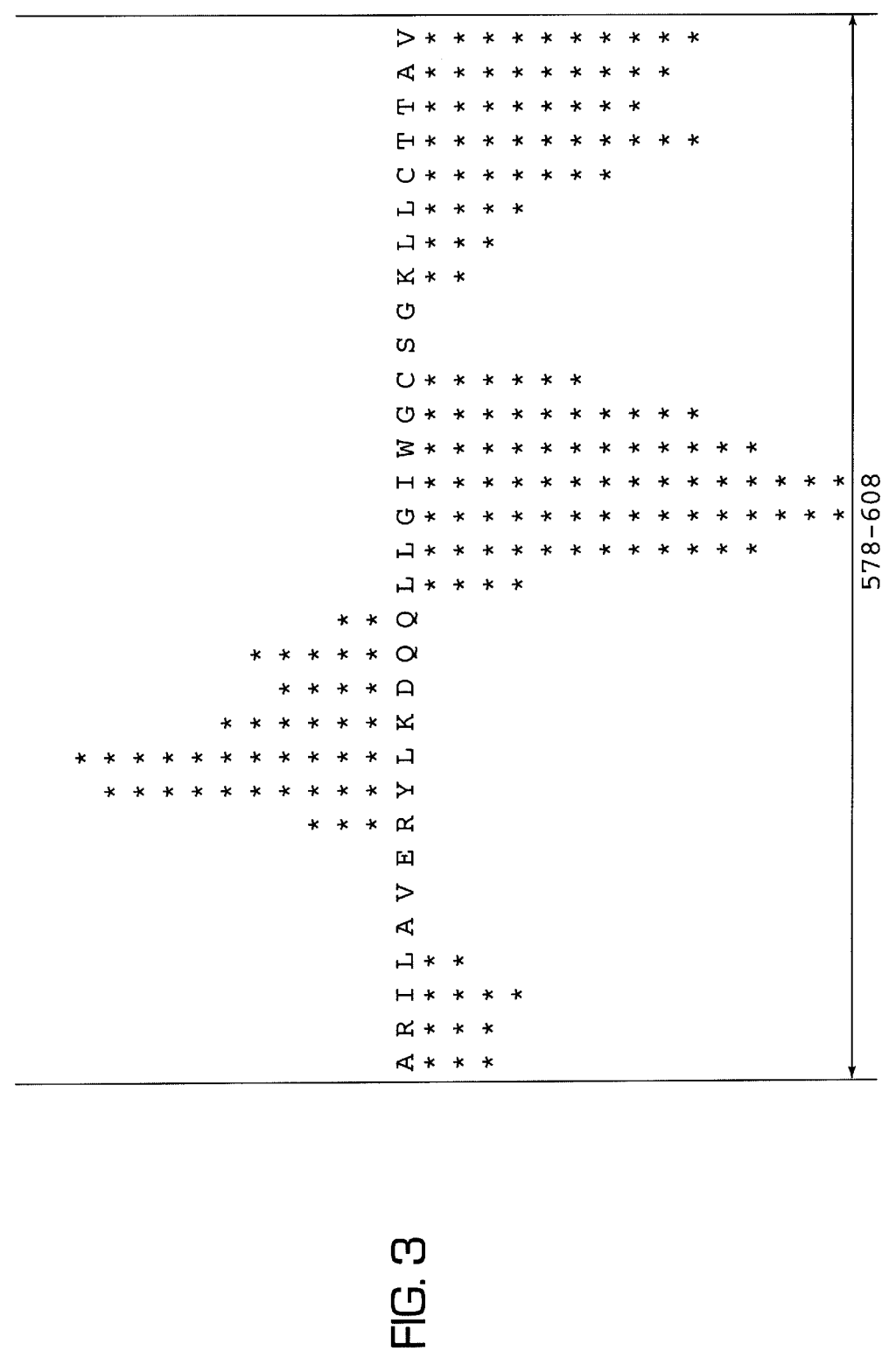

Hopp and Woods profiles of HIV(487–511) and HIV (469–511) are shown in FIG. 2 and a Hopp and Woods profile of HIV(578–608) is shown in FIG. 3.

As the lipid that is covalently bound to the amphipathic peptide, any lipid can be used, providing that means can be found to covalently couple the peptide to the lipid. One skilled in the art can readily determine if such means are present.

Examples of suitable lipids include phospholipids such as phosphatidylethanolamine (PE); sterols such as cholesterol; spingolipids such as sphingomyelin; glycolipids such as myeline; and other diacyl containing lipid structures, e.g., diacylamines.

Phospholipids are preferred, and phosphatidylethanolamine is especially preferred.

The peptide-lipid complex can be purified for use by removing unreacted components and detergent by dialysis. The material remaining in the dialysis bag after dialysis is the immunogen. No further purification needs to be performed.

In addition to preparing a peptide-lipid complex by covalently bonding the peptide to the lipid, naturally occuring complexes can also be used. Examples of such naturally occuring peptide-phospholipid complexes are complexes comprised of proteins linked to phosphatidylinositol.

The above-described peptide-lipid complex can be used alone as the immunogenic composite according to the present invention. However, in a preferred embodiment, the peptide-lipid complex is associated with a mixture of one or more lipids and one or more sterols.

The composite comprised of a peptide-lipid complex associated with a mixture of one or more lipids and one or more sterols can be produced by solubilizing all components, i.e. the peptide-lipid complex, the additional lipids, and the sterols, in a nontoxic detergent with a high critical micelle concentration. This solution is then dialyzed to remove the detergent. The result is a particulate suspension that is either vesicular in nature or what appears to be, when viewed by light microscopy, an amorphous particulate structure.

While not wanting to be bound by the following explanation, the nature of the peptide in the composite appears to be the factor determining the structure that results. That is, those peptides that are hydrophilic or neutral appear to more often form vesicular structures whereas those that are amphipathic appear to more often form amorphous, particulate aggregates.

The peptides are most probably associated with each other and with the additional lipids and sterols via hydrophobic interactions resulting from the acyl chains of the lipid to which the peptide is conjugated and the hydrophobic regions of the other lipids and sterols. However, as with membrane structures, ionic interactions and Van der Waals forces may also be involved.

Association can be tested by centrifugation of the dialyzed solution in an ultracentrifuge at high speed (100,000–300,000 xg). If the peptide-lipid complexes have been associated with the additional lipids and sterols to form an immunogenic composite according to the present invention, the peptide-lipid complexes will pellet along with the additional lipids and sterols.

The fate of peptide-lipid complexes can be monitored by, for example, radioactive label, fluorescent label, spectroscopy, thin layer chromatography or high pressure liquid chromatography.

More specifically, there are at least two ways to produce the composite comprised of a peptide-lipid complex associated with a mixture of one or more lipids and one or more sterols.

According to one method, derivatized lipid (for forming the peptide-lipid complex) is dissolved in detergent along with a mixture of one or more nonderivatized lipids and one or more sterols. A premade activated peptide is then added to the solution and allowed to react with the derivatized lipid to form a peptide-lipid complex. After completion of the reaction, the solution is dialyzed against an appropriate aqueous buffer to remove the detergent thereby forming a particulate suspension comprising the immunogenic composite.

The derivatized lipid for use in the above-described method is prepared according to conventional means such as those described for producing the peptide-lipid complex by itself. For example, if a cross-linking agent is used to form the peptide-lipid complex, the lipid is derivatized by joining a cross-linking reagent to the lipid. If necessary, the derivatized lipid is then extracted from the reaction mixture, also by conventional means.

The peptide is activated in accordance with the means used for joining the peptide to the lipid. For example, if a cross-linking agent is used to join the peptide to the lipid, the peptide is reduced with dithiothreitol by conventional means. The thus activated peptide is purified by conventional means such as affinity chromatography, or HPLC (high pressure liquid chromatography).

The detergent in which the thus-prepared derivatized lipid is dissolved along with one or more nonderivatized lipids and one or more sterols can be any nontoxic detergent with a high critical micelle concentration. By "high" critical micelle concentration, it is meant that the detergent can be removed by dialysis. Other detergents with "low" critical micelle concentrations, such as Triton X-100 or $C_{12}E_8$(N-dodecyloctaethylene monether), are also suitable but removal must be accomplished by means other than dialysis, such as, for example, by adsorbtion onto SM-2 beads. Suitable detergents having a high critical micelle concentration can readily be determined by one skilled in the art and examples include octyl-$\beta$-D-glucoside and octyl-$\beta$-D-thiogluco-pyranoside.

Octyl-$\beta$-D-glucoside is preferred.

The lipids and sterols are prepared for solubilization in detergent by first dissolving in an organic solvent that solubilizes but does not oxidize or in any way destroy the integrity of the phospholipid. Suitable organic solvents include diethyl ether, chloroform, benzene, and acetone.

The derivatized lipid, non-derivatized lipids, and sterols are used in a molar ratio of about 2:3:5, although a broad range of ratios can be used, and dissolved in the organic solvent at a concentration of about 10 mg (lipid and sterol)/ml (solvent), although a range of concentration ratios can be used.

The sample is then dried under a non-oxidizing atmosphere such as a nitrogen stream or argon.

The dried sample is resuspended in a suitable aqueous buffer such as an aqueous phosphate buffer or an aqueous citrate buffer, pH 4.5 to 6.5, at a concentration of about 4 mg(lipid and sterol)/1 ml (buffer) and the sample is sonicated at room temperature to form a particulate suspension of vesicles.

The detergent is then added to this sample and the sample is sonicated again at room temperature to dissolve all components.

The amount of detergent added is enough to solubilize the components in the mixture. A suitable amount is about 10:1 by weight based on the weight of total lipids and sterols. One skilled in the art can readily determine other suitable amounts of detergent.

To form the peptide-lipid complex, the activated peptide, prepared as described above, is added to the detergent mixture in an amount necessary to optimize coupling of the peptide to the derivatized lipid, for example in an amount of about 1:2 moles peptide per mole derivatized lipid. The pH and other reaction conditions are adjusted in accordance with the particular reaction to be carried out, and the peptide and derivatized lipid are allowed to react appropriately. The reaction conditions are readily determined by the skilled artisan. A suitable reaction time is generally overnight.

The dialysis is carried out according to conventional means for a period of time and with enough changes of buffer to remove essentially all of the detergent.

As the dialysis buffer, any aqueous buffer can be used that does not oxidize lipid or destroy the integrity of the immunogenic composite.

The result is a particulate suspension of the immunogenic composite comprising a peptide-lipid complex associated with a mixture of one or more lipids and one or more sterols.

According to a second method for preparing the immunogenic composite comprising a peptide-lipid complex associated with a mixture of one or more lipids and one or more sterols, a premade activated peptide, prepared as described for the first method, is added to a suspension containing vesicles comprised of derivatized lipid, also prepared as described for the first method, and a mixture of one or more lipids and one or more sterols, and the peptide is allowed to react with the derivatized lipid in the vesicles to form a peptide-lipid complex. An immunogenic composite with a peptide-lipid complex already in it can also be used as vesicles. After completion of the reaction, all of the components are solubilized in detergent, and the solution is dialyzed, as in the first method, against an appropriate aqueous buffer to remove detergent thereby forming a particulate suspension comprising the immunogenic composite.

In the second method the solution containing unilamellar vesicles is prepared in the same manner as the particulate suspension of vesicles is prepared in the first method. Peptide is reacted as above prior to the addition of detergent. Detergent is added at the end of the overnight coupling reaction. All other steps, times, concentrations, temperatures, pH's etc., are identical to those described in the first method.

More specifically, to form the peptide-lipid complex, the activated peptide is added to the mixture in an amount necessary to optimize coupling of the peptide to the derivatized lipid, for example in an amount of about 1:2 moles peptide per mole derivatized lipid. The pH and other reaction conditions are adjusted in accordance with the particular reaction to be carried out. The reaction conditions are readily determined by the skilled artisan. A suitable reaction time is generally overnight.

The detergent used to solubilize the components in the reaction mixture is the same as described above for the first method.

The sample is prepared for solubilization by adding detergent to the reaction mixture in an amount sufficient to solubilize the components of the mixture. A ratio of about 10 mg detergent to 1 mg total lipid and sterol is generally suitable. The sample is then sonicated to dissolve all components.

Once solubilized in detergent, dialysis is carried out as described above for the first method.

As the lipid and the peptide to be used in this embodiment of the invention, any lipid and any amphipathic peptide as described above for preparing the immunogenic composite comprising only an amphipathic peptide covalently bound to a lipid can be used.

Phospholipids are preferred and phosphatidylethanolamine is especially preferred.

The lipid component of the lipid/sterol mixture can be any lipid, providing it is not immunogenic, i.e. an animal does not demonstrate an immune response to the lipid either alone or in the composite. Nor should the lipid interfere with the ability of an animal to mount an immune response to the peptide.

One skilled in the art can readily determine whether a lipid is immunogenic by assaying for antibodies reactive against lipid in standard assays.

Further, the lipid component of the lipid/sterol mixture can be comprised of all one type of lipid or a mixture of two or more lipids, and the lipid may be the same as that present in the protein-lipid complex or it may be different.

Examples of lipids useful as the lipid component of the lipid/sterol mixture include phosphatidylserine (PS), phosphatidylcholine (PC), spingomyelin (SP), phosphatidylethanolamine (PE), phosphatidylinositol (PI), phosphatidylglycerol (PG); phosphatidic acid (PA), and cardiolipin.

Phospholipids are preferred.

As the sterol, any sterol can be used, providing that it does not solubilize lipid assemblies and is not immunogenic, i.e., it does not induce an immune response against itself and does not interfere with the ability of an animal to respond to the peptide, for example possess anti-inflammatory properties.

Mixtures of more than one sterol can be used, but use of only one sterol is preferred.

As used in the context of the lipid/sterol mixture, sterol means a class of abundant steroids containing an alcoholic hydroxyl group at the $C_3$ carbon and a branched aliphatic chain of 8 or more carbon atoms at the $C_{17}$ carbon. They occur either as free alcohols or as long chain fatty acid esters of the hydroxyl group at the $C_3$ carbon.

Examples of sterols that can be used in the mixture include cholesterol and lanosterol.

An especially preferred sterol is cholesterol.

The immunogenic composites, in second and third embodiments, are capable of selectively inducing or enhancing antibody production to a non-immunogenic hydrophilic and/or a non-immunogenic neutral peptide, as well as to a non-immunogenic amphipathic peptide.

One of these two immunogenic composites comprises a peptide-lipid complex which comprises a hybrid peptide covalently bound to a lipid and said hybrid peptide comprises a non-immunogenic amphipathic peptide covalently bound to one peptide selected from the group consisting of: (a) a non-immunogenic hydrophilic peptide; (b) a non-immunogenic neutral peptide; (c) a non-immunogenic amphipathic peptide; and (d) a hybrid peptide comprising any combination of two or more of the above-defined peptides (a), (b) and (c). In a preferred embodiment, the peptide-lipid complex is associated with a mixture of one or more lipids and one or more sterols.

This immunogenic composite, either the peptide-lipid complex alone or associated with a mixture of one or more lipids and one or more sterols, can be prepared in the same manner as described above for the immunogenic composite comprising a non-immunogenic amphipathic peptide covalently bound to a lipid, except that the peptide in the peptide-lipid complex comprises a hybrid peptide comprising a non-immunogenic amphipathic peptide covalently bound to one of: (a) a non-immunogenic hydrophilic peptide; (b) a non-immunogenic neutral peptide; (c) a nonimmunogenic amphipathic peptide; and (d) a hybrid peptide comprising any combination of two or more of the above-defined peptides (a), (b) and (c).

The peptides forming either of the hybrid peptides are covalently bonded together, preferably end-to-end.

Further, since amino to amino and carboxyl to carboxyl bonds are usually unstable in an aqueous environment, end-to-end bonding is preferably by amino ends to carboxyl ends.

As the hydrophilic or neutral peptide, any hydrophilic or neutral peptide that meets the above definitions can be used. Also, if the immunogenic complex is to be used as a vaccine, the peptide should not be toxic or otherwise detrimental to the health of the animal.

Examples of hydrophilic peptides include HIV(469–485), HIV(500–511) and HIV(647–659).

The primary sequences of these peptides are shown in FIG. 1.

Figure 4:
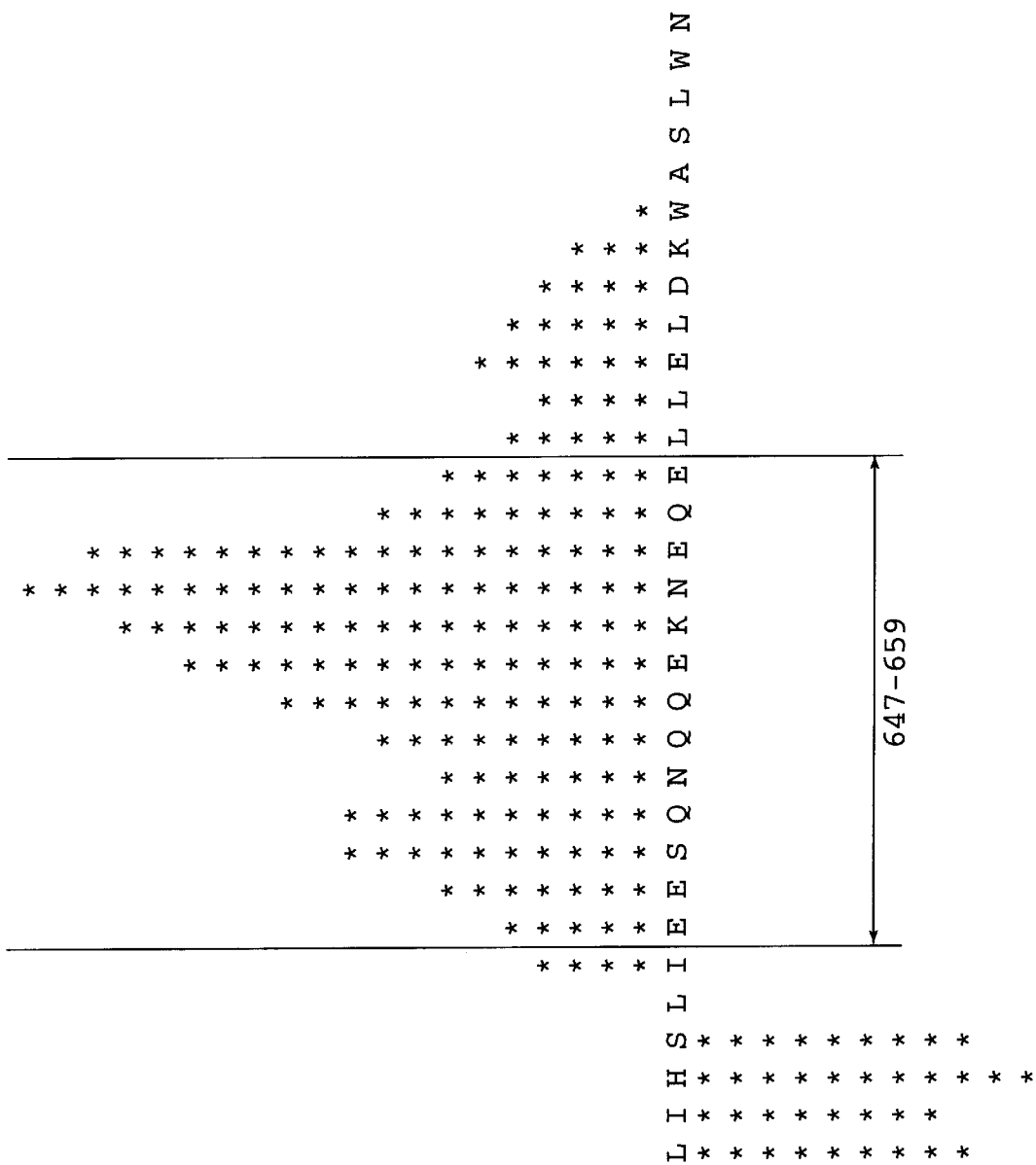

Hopp and Woods profiles of HIV(469–485) and HIV (500–511) are shown in FIG. 2 and a Hopp and Woods profile of HIV(647–659) is shown in FIG. 4.

An example of a neutral peptide is $(NANP)_n$.

Figure 5:
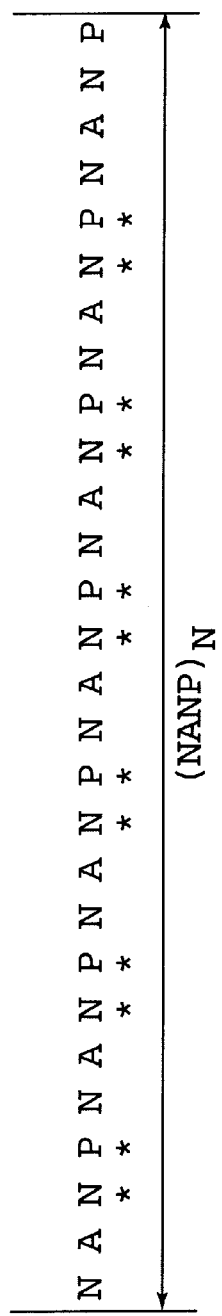

The primary sequence of $(NANP)_3$ is shown in FIG. 1 and a Hopp and Woods profile is shown in FIG. 5.

The amphipathic peptide for use in the hybrid peptide is the same as that described above for the first embodiment of the immunogenic composite.

In particular, the amphipathic peptides $T_2$ (HIVenv (112–124), H-E-D-I-I-S-L-W-N-Q-S-L-K) and $T_1$ (HIVenv (428–443), L-Q-I-I-N-M-W-Q-E-V-L-A-M-Y-A-$NH_2$) (Cease, et al., *Proc. Natl. Acad. Sci. U.S.A.* 84:4249–4253 (1987)) are useful in conjunction with hydrophilic or neutral peptides from HIV(e.g. HIV(299–329)) for inducing an immune response to these non-immunigenic peptides.

The hybrid peptides can be made by any one of the accepted state of the art peptide synthesizing reactions, either manually or in an automated peptide synthesizer. Also hybrid peptides can be produced by standard state of the art genetic engineering procedures. In addition hybrid peptides can be produced by chemical or enzymatic buildup from peptide fragments or by cleavage of larger hybrid polypeptides or proteins.

Further, according to this embodiment of the invention, any number and types of peptides can be fused together to give an immunogenic composite to which multiple antibodies are made. Of course, there is a practical limit on the size of the ultimate peptide in that there are technical limitations to the length of creating a synthetic peptide, as well as structural problems based on peptide folding should the peptide be too long or two short. These limitations can readily be determined by the skilled artisan.

The thus prepared hybrid peptide can be bonded to the lipid to form an immunogenic peptide-lipid complex by the same methods described above for the first embodiment of the immunogenic composite without regard to which of the peptides forming the hybrid peptide forms the covalent bond to the lipid.

Examples of hybrid peptides include: (a) HIV(469–511), comprised of the non-immunogenic hydrophilic peptide HIV(469–485) and the non-immunogenic amphipathic peptide HIV(487–511), and (b) HIV(487–511), comprised of the non-immunogenic hydrophilic peptide HIV(500–511) and the nonimmunogenic amphipathic peptide HIV (487–499).

When HIV(469–511) is made part of an immunogenic composite according to the present invention antibodies are produced against the non-immunogenic hydrophilic peptide HIV(469–485) (as well as against the peptides HIV (487–511), (469–511), and (500–511)).

When HIV(487–511) is made part of an immunogenic composite according to the present invention, antibodies are produced against the non-immunogenic hydrophilic peptide HIV(500–511) (as well as against the peptides HIV (487–511) and (469–511)).

The other of the two composites according to the present invention which are capable of selectively inducing or enhancing antibody production to a non-immunogenic hydrophilic and/or a non-immunogenic neutral peptide, as well as to a non-immunogenic amphipathic peptide, comprises a first peptide-lipid complex, wherein the peptide is at least partly comprised of an amphipathic peptide, and one or more additional peptide-lipid complexes associated with a mixture of one or more lipids and one or more sterols.

The first peptide-lipid complex comprises one of the above-described immunogenic complexes having an amphipathic peptide associated therewith.

That is, the first peptide-lipid complex can be either the above-described peptide-lipid complex comprising a non-immunogenic amphipathic peptide covalently bound to a lipid or the above-described hybrid peptide-lipid complex comprising a hybrid peptide covalently bound to a lipid, wherein the hybrid peptide comprises a non-immunogenic amphipathic peptide covalently bound to one of: (a) a non-immunogenic hydrophilic peptide; (b) a non-immunogenic neutral peptide; (c) a non-immunogenic amphipathic peptide; and (d) a hybrid peptide comprising any combination of two or more of the above-defined peptides (a), (b) and (c).

The one or more additional peptide-lipid complexes comprises one or more of the following complexes: (1) a non-immunogenic hydrophilic peptide covalently bound to a lipid; (2) a non-immunogenic neutral peptide covalently bound to a lipid; (3) a non-immunogenic amphipathic peptide covalently bound to a lipid; and (4) a hybrid peptide covalently bound to a lipid, wherein the hybrid peptide comprises a non-immunogenic amphipathic, hydrophilic, or neutral peptide covalently bound to a peptide selected from: (a) a non-immunogenic hydrophilic peptide; (b) a non-immunogenic neutral peptide; (c) a non-immunogenic amphipathic peptide; and (d) a hybrid peptide comprising any combination of two or more of the above-defined peptides (a), (b) and (c).

That is, the one or more additional peptide-lipid complexes can be any of those described previously, but in addition can include peptide-lipid complexes that do not have any amphipathic peptides.

According to this embodiment of the present invention, antibodies can be made to peptide-lipid complexes which are not, in and of themselves, capable of being immunogenic, i.e., any complex that does not include an amphipathic peptide.

Thus, for example, an immunogenic composite comprising a mixture of one or more lipids and one or more sterols having associated therewith one peptide-lipid complex wherein the peptide is an amphipathic peptide such as $T_2$ or $T_1$ from HIV and another peptide-lipid complex wherein the peptide is a hydrophilic peptide such as HIV(299–329), will induce antibodies not only to the amphipathic peptides $T_2$ or $T_1$, but also to the hydrophilic peptide HIV(299–329). If another peptide-lipid complex is included, antibodies to the peptide(s) in the additional complex will be induced.

This immunogenic composite, according to the third embodiment of the present invention, can be prepared in the same manner as described above for the other immunogenic composites, except that two or more peptide-lipid complexes are associated with the mixture of one or more lipids and one or more sterols. This result can be achieved by, for example, reacting more than one peptide at the same time with the derivatized lipid, according to either of the two above-described methods.

The hydrophilic or neutral peptide for use in peptide-lipid complexes comprising a non-immunogenic hydrophilic peptide covalently bound to a lipid, a non-immunogenic neutral peptide covalently bound to a lipid and a hybrid peptide covalently bound to a lipid, is the same as that described above for the hybrid peptide, and the amphipathic peptide for use in any of the peptide-lipid complexes employing amphipathic peptides is the same as that described above for the first embodiment of the immunogenic composite.

The hydrophilic and neutral peptides are covalently bonded to the lipid in the same manner as described above for the amphipathic peptide-lipid complex.

Further, according to the present invention, any two or more of the above-described immunogenic composites can be combined in admixture to give an immunogenic composition. This approach can also be used to produce antibodies to more than one peptide.

The immunogenic composites according to the present invention are useful as immunogens. Practical applications include non-clinical as well as clinical uses. Examples of non-clinical uses include immunization for the purposes of raising monoclonal antibodies and producing antibodies to defined and specific epitopes for use in diagnostics.

Examples of clinical uses include the preparation of vaccines and induction of systemic or mucosal antibodies against sperm for use as a contraceptive.

Accordingly, the present invention also provides a pharmaceutical composition and a method for selectively inducing or enhancing antibody production.

The pharmaceutical composition comprises a mixture of one or more of the above-described immunogenic composites and a pharmaceutically acceptable carrier, diluent or excipient.

The method comprises administering a pharmaceutically effective amount of the pharmaceutical composition to a host in which an immune response is the normal means of defense to infection by foreign materials.

Examples of suitable pharmaceutically acceptable carriers, diluents and excipients include, for example, balanced salt solutions, any aqueous buffer, water and any of numerous inert carriers.

The dosage form can be oral, nasal, intramuscular, intravenous, intraperitoneal, intraocular, subcutaneous, intravaginal, or on any mucosal surface.

Although the dosage varies with the nature of the infectious agent against which immunity is sought and/or with the nature of the peptide against which antibody production is sought, one skilled in the art can readily determine suitable dosages.

A suitable dosage in mice varies from about 10 to about 100 μg per gm body weight.

EXAMPLES

The invention will now be described by reference to specific examples, but the invention should not be construed as being limited thereto.

Unless otherwise specified, all percents, ratios, etc. are by weight.

Example 1

PRODUCTION OF IMMUNOGENIC COMPOSITE CAPABLE OF SELECTIVELY INDUCING ANTIBODY PRODUCTION TO NON-IMMUNOGENIC AMPHIPATHIC PEPTIDES

Initial Preparations Of Peptide-lipid Complex

I. Joining of crosslinking reagent to phosphotidylethanolamine was accomplished according to the method of Martin and Papahadjopoulos (*J. Biol. Chem.* 257:286–288 (1982)) as follows:

A. Reagents
  1. Succinimidyl-4-(p-maleimidophenyl) butyrate (SMPB)
  2. Phosphatidylethanolamine (PE)
  3. Anhydrous methanol
  4. Triethylamine B. Procedure
  1. Reagents were reacted for two hours at room temperature under $N_2$ (e.g. 2 ml methanol, 5 μl triethylamine, 17 mg SMPB, added to 25 mg dry PE).
  2. Methanol was removed from the reaction products with a stream of $N_2$.
  3. 2 ml $CHCl_3$ was added and the mixture was extracted 2 times with 2 ml of 1% NaCl in $H_2O$ by centrifuging at 1500 RPM, 5 min. All procedures in this step were performed under $N_2$.
  4. Chromatography on a silica gel column was then performed as follows:
    a. The column was washed with 50 ml $CHCl_3$.
    b. The sample in 5 ml $CHCl_3$ was loaded on the column, followed by 10 ml each of $CHCl_3$: MeOH 40:1, 30:1, 25:1, 20:1, 15:1, and then 40 ml 10:1 while collecting 5 ml fractions.
  5. Thin layer chromatography of the silica gel column fractions (solvent-$CHCl_3$:MeOH:$H_2O$, 65:25:4) was then conducted. The coupled cross linker and phospholipid (MPB-PE) that eluted in the early 10:1, $CHCl_3$:MeOH fractions showed a single spot comigrating with a PE standard. The derivatized PE spot was ninhydrin negative, iodine positive. The PE standard spot was ninhydrin positive. Silica gel column fractions containing MPB-PE were pooled and stored under $N_2$ at −20° C.
  6. Phospholipid was quantitated by the method of Bartlett (*J. Biol. Chem.* 234:466 (1959)). The ave. yield was 50%.

II. Reduction of peptide according to Roche procedure

A. Reaction
  1. The amphipathic peptide HIV(487–511), HIV(469–511), or HIV(578–608), prepared by solid-phase procedures (Yarney and Marrifield. In "The Peptide: Analysis, Synthesis, Biology." Academic Press, N.Y. Vol. 2 1–284.) was dissolved in 1M acetic acid (HAc) (e.g. 2 mg peptide in 1 ml HAc).
  2. Dithiothreitol (DTT) was added to 100 mM conc.
  3. The sample was degassed, nitrogenized, and then incubated in a screw-cap tube at 37° for 3 hours.

B. Affinity chromatography on Bondelute column (3cc column obtained from Analytichem International C18, part 607203).
  1. The column was washed with 2 vols 100% MeOH, then 10 vols 1MHAc.
  2. The peptide was applied to the Bondelute column.
  3. The column was washed with 5 volumes 1M HAc, then 5 vols 0.02% trifluoracetic acid (TFA).

4. The sample was eluted with 5 volumes 60% acetonitrile, 0.02% TFA.
5. The eluted sample was lyophilized overnight and stored at −20° C. Essentially complete recovery was obtained.

III. Preparation of immunogenic composites comprising peptide-lipid complex associated with a mixture of lipids and a sterol (cholesterol)

A. Lipids—MPB-PE, sphingomyelin (SP), phosphatidylcholine (PC), phosphatidylserine (PS).

Sterol—cholesterol (Ch).

B. Procedure
1. The lipids and cholesterol (Ch) were dissolved in ether (10 mg/ml) at a molar ratio of MPB-PE:SP:PC:PS:Ch of 2:1:1:1:5.
2. The sample was dried under a nitrogen stream.
3. The dried sample was resuspended in buffer (20 mM citric acid, 35 mM disodium phosphate, 108 mM NaCl, 1 mM EDTA, pH 4.5) at 4 mg lipid and cholesterol/ml.
4. The sample was sonicated to form a particulate suspension.
5. Octyl-β-D-glucoside (10 mg/mg lipid and sterol) was added to the sonicated sample.
6. The sample was again sonicated to dissolve all lipid.
7. The sample was stored under $N_2$ in the dark.

IV. Coupling of peptide to lipid mixture containing derivatized phosphatidylethanolamine (MPB-PE)

A. Procedure
1. Premade reduced peptide from step II above was added to the lipid/sterol mixture from step III above containing MPB-PE (MPB-PE molar concentration was 2× molar concentration of peptide) at pH 4.5.
2. The pH was adjusted to 6.5 with 1N NaOH.
3. The MPB-PE and peptide in the mixture were allowed to react under $N_2$ at room temperature overnight.
4. The mixture was dialyzed against several changes of phosphate buffered saline at 4° C., pH 7.2.
5. The immunogenic composite comprising the protein-lipid complex associated with a mixture of lipids and cholesterol was recovered from the dialysis bag and stored refrigerated (4° C.).

Example 2

PRODUCTION OF IMMUNOGENIC COMPOSITES CAPABLE OF SELECTIVELY INDUCING ANTIBODY PRODUCTION TO NON-IMMUNOGENIC HYDROPHILIC PEPTIDES

Immunogenic composites capable of selectively inducing non-immunogenic neutral or hydrophilic peptides were made in two ways:
(1) constructing the neutral or hydrophilic peptide contiguous to an amphipathic peptide to form a hybrid peptide by standard procedures as described in, for example Varney, G. and Marrifield, R. B. in *The Peptides: Analysis, Synthesis, Biology*, (E. Gross & J. Meinhofer, Eds.) Academic Press, N.Y. 2:1–284, reducing the hybrid peptide, and then covalently bonding the reduced hybrid peptide to a derivatized lipid present in solution with other lipids and cholesterol as described above in Example 1 and dialyzing as described in Example 1 to form an association of the hybrid peptide-lipid complex with a mixture of lipids and cholesterol; or
(2) covalently bonding a mixture of a reduced non-immunogenic neutral or hydrophilic peptide and a reduced amphipathic peptide to a derivatized lipid present in solution with other lipids and cholesterol as described in Example 1, and dialyzing as described in Example 1 to form an association of both peptide-lipid complexes with a mixture of lipids and a sterol.

Using method 1, immunogenic composites were prepared using the HIV peptides (487–511), (469–511) and (578–608).

Example 3

ANTIBODY PRODUCTION BY IMMUNOGENIC COMPOSITES OF EXAMPLE 1

Six to eight week old female inbred mice were immunized intraperitoneally with the immunogenic composites prepared in Example 1 (and composites which were prepared as in Example 1 but where the peptide was $(NANP)_3$, IL-2(1-12)-trans (the primary amino acid sequence is shown in FIG. 1), HIV env(469–485), HIV env(500–511) and HIV env (578–608) all of which are either hydrophilic or neutral). Each was used in an amount equivalent to 30 μg of peptide on days 0 and 14. On day 28 mice were immunized with the composites in an amount equivalent to 7.5 μg of peptide. Mire were bled from the retroorbital socket on days 0, 14, 28 and 42. Following collection, the blood was allowed to clot and the serum was separated by centrifugation. Serum was tested for antibody by the enzyme-linked immunosorbent assay (ELISA) described below.

ELISA—Direct Binding Assay

A. Plate Coating
1. Wells were coated with antigen (whichever peptide was used to immunize or to test against) diluted to about 0.5 to 1 μg/ml in bicarbonate-carbonate saline, pH 9.6.
2. Wells were coated with BSA or gelatin diluted to 10× the concentration of antigen for control.
   (a) 100 μl of BSA in bicarbonatecarbonate buffer were placed in each well.
   (b) Plates were dried overnight at 37° C.
   (c) Wells were washed 5 times with $dH_2O$ or PBS/tween (3×).

B. Blocking Reaction
1. 200 μl of 1% gelatin in Borate Buffered saline, pH 8.2 or 1% BSA in PBS, pH 7.0 (no tween) were placed in each well.
   (a) Plates were covered and incubated 1 hour at 37° C.
   (b) After incubation, wells were washed 5 times with 1× PBS/tween.

C. Binding Reaction
Serum containing antibody was diluted (a series of 2-fold dilutions starting at 1:100) with 1% BSA in PBS (0.5 M NaCl) and tween, pH 6.5.
   (a) 100 μl of sample was added per well and the plates were covered.
   (b) Samples were incubated at RT on a shaker for 2 hours.
   (c) Plates were washed 5 times with PBS/tween.

D. Detection Reaction for Mouse Antibodies
1. Affinity purified goat antimouse IgG and IgM-HrP (BOEH. MANN. Cat. #605–26) was diluted 1:1000 in 1% BSA in PBS/tween, pH6.
   (a) 100 μl of the solution was added to each well, and the plates were covered and protected from light.

(b) The solutions were incubated at RT on a shaker for 2 hours.

(c) The plates were washed 5 times with PBS/tween.

E. Substrate Reaction 1. 0-phenylenediamine dihydrochloride (SIGMA #P-1526) was mixed in 0.1M citrate buffer, pH 4.5 to give a final concentration of 0.4 mg/ml. 4 μl of 30% $H_2O_2$ was added for every 10 ml of buffer.

(a) 100 μl of the solution was added to each well, and the plates were protected from light.

(b) The solution was allowed to react for 15 min. at RT on a shaker.

(c) The extent of antibody binding was determined by measuring the optical density at 488 nm.

Solutions for ELISA

Bicarbonate-carbonate (B-C) Buffer—10×

0.5 M $NaHCO_3$ 0.5 M $Na_2CO_3$ mix in approximately equal volumes until pH=9.6.

Bicarbonate-carbonate Saline 25 mls 10× B-C buffer 7.5 mls 5M NaCl 1.8 mls 1M $NaN_3$ bring to 250 mls with distilled $H_2O$ and filter (0.20 μ pore size).

1% BSA in PBS, pH 7.0

20 mls 0.5 M $NaPO_4$ buffer, pH 7.0

15 mls 5M NaCl 0.5 ml 1M $MgCl_2$ 1.0 ml 0.5M $CaCl_2$ 5.0 gms Bovine serum albumin, Fraction V, Reagent Grade Bring to 500 mls with $dH_2O$ and filter (0.45 μ pore size). Store at 4° C.

0.5 M $NaPO_4$ Buffer

1. $Na_2HPO_4.7H_2O$ (dibasic)—67 gm/500 ml

2. $NaH_2PO_4.H_2O$ (monobasic)—34.5 gm/500 ml

Mix "1" and "2" together until desired pH is reached. For pH 6.5 add approximately equal volumes of "1" and "2" For pH 7.0 add ~500 ml "1" to ~200 ml "2".

1% BSA in PBS/tween, PH 6.5

20 mls 0.5 M $NaPO_4$ buffer, pH 6.5

15 mls 5M NaCl 0.5 ml 1M $MgCl_2$ 1.25 ml 20% Tween-20

1.0ml 0.5M $CaCl_2$ 5.0 gm Bovine serum albumin, Fraction V, Reagent Grade

Bring to 500 mls with $dH_2O$ and filter (0.45 μ pore size). Store at 4° C.

1% BSA in PBS (0.5 M NaCl) and tween, pH 6.5

20 mls 0.5M $NaPO_4$ buffer, pH 6.5

50 mls 5M NaCl 0.5 ml 1M $MgCl_2$ 1.25 ml 20% Tween-20

1.0 ml 0.5M $CaCl_2$ 5.0 gm Bovine serum albumin, Fraction V, Reagent grade

Bring to 500 mls with $dH_2O$ and filter (0.45 μ pore size). Store at 4° C.

0.1M Citrate Buffer, pH 4.5

7.35 gm trisodium citrate ($Na_3C_6H_5O_7.2H_2O$)

5.25 gm citric acid monohydrate

Bring to 500 ml, pH 4.5.

2.5M $H_2SO_4$ and 50 mM $Na_2S_2O_5$ (sodium meta bisulfite)

69.4 ml conc $H_2SO_4$ 4.75 gm sodium meta bisulfite

Mix each separately in $dH_2O$. Add together.

Bring to 500 mls with $dH_2O$ and filter (0.45 μ pore size). Store at 4° C.

1% gelatin in BBS, pH 8.2

10 gms gelatin 6.18 gm $H_3BO_3$ 9.54 gm $Na_2B_4O_7.10H_2O$ 4.38 gm NaCl

Bring to 1 liter with $dH_2O$ and filter (0.45 μ pore size). Store at RT.

2% BSA in PBS (1M NaCl) and 0.15% Tween-20, pH 6.5

10 gms Bovine serum albumin, Fraction V, Reagent grade 100 mls 5M NaCl 20 mls 0.5M $NaPO_4$ buffer, pH 6.5

0.5 ml 1M $MgCl_2$ 1.0 ml 0.5M $CaCl_2$ 3.75 ml 20% Tween-20

Bring to 500 mls with $dH_2O$ and filter (0.45 μ pore size). Store at 4° C.

The results for sera obtained on day 42 after initial immunization are shown in Table 1 below.

TABLE 1

Antibody Titers Of Mice Immunized With Various Peptide-Lipid Conjugates

| Peptide | $Log_{10}$ Antibody Titer to Immunizing Peptide |
| --- | --- |
| Hydrophilic or Neutral | |
| (NANP)₃ | 0.0(6)* |
| IL-2(1-12)-trans | 1.2 ± 1.3(6) |
| HIV env. (469–485) | 0.0(5) |
| HIV env. (500–511) | 0.0(5) |
| HIV env. (647–659) | 0.0(5) |
| Amphipathic | |
| HIV env. (469–511) | 4.4 ± 0.5(5) |
| HIV env. (487–511) | 4.3 ± 0.8(4) |
| HIV env. (578–608) | 4.4 ± 0.4(5) |

*the figure in parenthesis indicates the number of mice per group.

The results clearly show that complexing an amphipathic peptide with phospholipid and associating it with additional phospholipid and cholesterol induces a significant immune response when injected into mice. This is in contrast to the results with neutral and hydrophilic peptides which do not induce an immune response in mice even when covalently linked to phosopholipid and complexed with additional phospholipid and cholesterol.

That the amphipathic peptide is not by itself immunogenic is seen from the data set forth in Table 4 of Example 5.

Example 4

ANTIBODY PRODUCTION BY IMMUNOGENIC COMPOSITES OF EXAMPLE 2

Mice were immunized with the immunogenic composites prepared in Example 2 and with composites prepared as in Example 1 but using HIV peptides (469–485) and (500–511). Antibody titers were determined as in Example 3.

The results are shown in Table 2 below.

TABLE 2

Immune Response To Nonimmunogenic Hydrophilic Peptides Of HIV Envelope Protein When Synthesized Contiguous With A Hydrophobic Sequence From The Same Protein

| Immunizing Peptide | $Log_{10}$ Antibody Titer to | | | |
|---|---|---|---|---|
| | 469–485 | 487–511 | 469–511 | 500–511 |
| 469–485(5)* | 0.0 | 0.0 | 0.0 | 0.0 |
| 487–511(5) | 0.0 | 5.3 ± 0.2 | 3.2 ± 0.8 | 3.2 ± 0.5 |
| 469–511(5) | 2.8 ± 0.7 | 3.2 ± 0.8 | 4.4 ± 0.5 | 3.1 ± 0.8 |
| 500–511(5) | 0.0 | 0.0 | 0.0 | 0.0 |

*the figure in parenthesis indicates the number of mice per group.

The results show that when non-immunogenic peptides (469–486, 500–511) were synthesized contiguous to amphipathic peptides (in 469–511 and 487–511) the mice were able to produce antibodies to the neutral and hydrophilic regions. Thus, these regions became immunogenic when incoporated into larger amphipathic peptides, complexed to phospholipid, and associated with additional phospholipid and cholesterol.

As a method of adding amphipathic structures, purified viral glycoproteins (S. Gould-fogerite and J. Mannino, *Anal. Biochem.* 148:15–26 (1985)) were added, by mixing with dissolved peptide-lipid, phospholipids and simple lipids, to some of the nonimmunogenic peptide-phospholipid complexes at 1/200 of their naturally occurring concentrations and the composite was dialyzed overnight at room temperature against 3 changes of phosphate-buffered saline pH 7.2.

The results are shown in Table 3 below.

TABLE 3

Effect Of Addition Of Highly Immunogenic Proteins To Liposomes Containing Nonimmunogenic Peptide - Phospholipid Conjugates

| Peptide | Viral Glycoproteins | $Log_{10}$ Antibody Titer to Immunizing Peptide |
|---|---|---|
| — | Influenza | 0.0* (6)** |
| — | Sendai | 0.0(6) |
| (NANP)$_3$ | — | 0.0(6) |
| (NANP)$_3$ | Influenza | 3.4 ± 0.2(6) |
| (NANP)$_3$ | Sendai | 3.7 ± 0.5(5) |
| IL-2(1-12)-trans | — | 1.2 ± 1.3(6) |
| IL-2(1-12)-trans | Influenza | 3.5 ± 0.3(6) |
| IL-2(1-12)-trans | Sendai | 4.1 ± 0.4(6) |

Antibody titers to Sendai and influenza glycoproteins were greater than $log_{10}4.5$ in all mice tested.
*No antibodies were detected to either (NANP)$_3$ or IL-2(1-12)-trans
**The figure in parenthesis indicates that number of mice per group.

As shown above in Table 3, the addition of amphipathic molecules in the form of viral glycoproteins results in the production of antibodies to two previously nonimmunogenic peptides. In each case, the increase in antibody titer is greater than 2 logs.

Therefore, when neutral or hydrophilic peptides are completed to phospholipid and added to preparations containing amphipathic structures and additional phospholipid and cholesterol, they become immunogenic.

Example 5

IMPORTANCE OF COUPLING NON-IMMUNOGENIC PEPTIDES TO LIPIDS IN ORDER TO PRODUCE IMMUNOGENIC RESPONSE

Table 4 below shows the importance of coupling the amphipathic peptide to lipids in order to produce an immunogenic structure.

TABLE 4

| Peptide | $Log_{10}$ Antibody Titer to Immunizing Peptide |
|---|---|
| HIV env. (487–511) - mixed lipid conjugate* | 5.3 ± 0.2(5) |
| HIV env. (487–511) - mixed lipid conjugate** | 5.4 ± 0.3(5) |
| HIV env. (487–511) - mixed lipid free*** | 0.0(5) |
| HIV env. (487–511) in sterile PBS*** | 0.0(5) |

Antibody titers of mice immunized with HIV env. (487–511) conjugated to phospholipid by the following methods:
*MPB-PE was mixed with the other phospholipids and cholesterol in small unilamelar vesicles and reacted with peptide overnight at room temperature. The reaction mixture was dissolved with octyl-β-D-glucoside (10 mg/mg lipid) and dialyzed against CMF-PBS to form a peptide phospholipid complex.
or
**MPB-PE and mixed phospholipids and cholesterol were dissolved in Octyl-β-D-glucoside (10 mg octyl-β-D-glucoside/mg lipid), reacted with peptide overnight at room temperature and subsequently dialyzed against CMF-PBS to form a peptide phospholipid complex.
or
***uncomplexed and mixed with preformed lipid-cholesterol structures or uncomplexed and injected in sterile saline.

The results in Table 4 show that when the peptide is complexed to phospholipid as a lipid and associated .with additional phospholipid as a lipid and cholesterol as a sterol, an immunogenic composite is produced. This composite is significantly immunogenic regardless of whether the initial coupling is to MPB-PE already associated in a structure with other lipid and cholesterol or free in solution by virtue of being dissolved in octyl-β-D-glucoside. In contrast, if the peptide is mixed with preformed lipid-cholesterol structures, but not complexed with phospholipid no immune response is observed. Furthermore, no immune response is observed if solubilized 487–511 is injected into an animal in sterile PBS. Therefore, it is of utmost importance for the amphipathic peptide to be covalently linked to the lipid for it to be immunogenic.

Example 6

CONSTRUCTION OF A SYNTHETIC VACCINE AGAINST MALARIA

The peptide (NANP)$_n$ is a repeated peptide of great immunological significance in protection from infection by malaria sporozoites. However, (NANP)$_n$ is a neutral peptide and is not in and of itself immunogenic in most animals.

Recently, an immunologically important amphipathic peptide, also from the malaria sporozoite, has been identified (M. F. Good, et al., *Science* 235:1059–1062 (1987). This amphipathic peptide has the following sequence: P-S-D-K-H-I-E-Q-Y-L-K-K-I-K-N-S-I-S.

The vaccine would be produced as follows.

The fused peptide, P-S-D-K-H-I-E-Q-Y-L-K-K-I-K-N-S-I-S-(NANP)$_n$, n=3, is constructed in a synthetic protein synthesizer.

The fused peptide is then reduced with dithiothreitol and solubilized in a non-ionic detergent with a high critical micelle concentration, such as octyl-β-D-glycoside, along with derivatized phosphatidylethanolamine (PE), a mixture of lipids comprising, for example sphingomyelin, phosphatidylserine, and phosphatidylcholine, and cholesterol as a sterol.

The fused peptide is cross-linked to the derivatized PE by one of the known methods, such as by that of Martin and Papahadjopoulis (1982). *J. Biol. Chem.* 257:286–288.

The solution is dialyzed against phosphate-buffered saline, pH 7.2 to give a particulate suspension of an immunogenic composite and the suspension is adjusted to the appropriate concentration in phosphate buffered saline.

Example 7

CONSTRUCTION OF A SYNTHETIC VACCINE AGAINST HIV III

The following non-immunogenic hydrophilic peptides of immunologic significance are known for HIV III: (299–329) H-R-P-N-N-N-T-R-K-I-R-I-R-E-P-E-R-A-E-K-I-E-N-M-R-Q-C-$NH_2$ and (735–752) D-R-P-E-G-I-E-E-E-G-G-E-R-D-R-S.

The following immunologically important amphipathic peptides also from HIV III have recently been described by K. B. Cease (*Proc. Nat. Acad. Sci. USA* 84:4249–4253 (June 1987)): $T_2$ (HIVenv(112–124), H-E-D-I-I-S-L-W-H-Q-S-L-K) $T_1$ (HIVenv(428–443), L-Q-I-I-N-M-W-Q-E-V-L-A-M-X-A-$NH_2$) and by Putney et al. (*Science* 234:1392–1395 (December 1986)): (HIV(340–368) H-N-N-T-L-K-Q-I-D-S-K-L-R-E-Q-F-G-N-N-L-Q-S-S-G-C-$NH_2$).

One or more vaccines would be produced according to the procedures of the present invention by forming immunogenic composites with protein-lipid complexes wherein the protein is as follows: 340–368 alone; 340–368 fused to 487–511; 299–324 fused to 340–368; 299–324 fused to 487–511; 299–324 fused to 578–608; and 340–368 fused to 578–608.

More preferably, immunogenic composites are formed which include more than one of the above-described protein-lipid complexes, e.g. 340–368 fused to 487–511 and 299–324 fused to 378–608 are included in the same composite.

While the invention has been described in detail and with reference to specific embodiments thereof, it will be apparent to one skilled in the art that various changes and modifications can be made therein without departing from the spirit and scope thereof.

What is claimed is:

1. An essentially pure immunogenic composition comprising:

(A) a lipid, which is one member selected from the group consisting of a phospholipid, sphingolipid, and sterol, each of which is a component of membranes of eukaryotic or prokaryotic cells, covalently bound to (B) an amphipathic peptide that primes homologous helper T-cells and that when administered by itself to a animal does not stimulate production of anti-peptide antibody in said animal;

wherein, when said lipid is a phospholipid or sphingolipid, said amphipathic peptide is covalently bound to a head group of said phospholipid or sphingolipid via a cross-linker, and wherein said immunogenic composition selectively induces antibody production in said animal to said amphipathic peptide.

2. The essentially pure immunogenic composition of claim 1, further comprising at least two additional lipids, at least one of which is a sterol.

3. An essentially pure immunogenic composition comprising:

(A) a lipid, which is one member selected from the group consisting of a phospholipid, sphingolipid, and sterol, each of which is a component of membranes of eukaryotic or prokaryotic cells, covalently bound to (B) a first hybrid peptide that is (1) an amphipathic peptide that primes homologous helper T-cells and that when administered by itself to an animal does not stimulate production of anti-peptide antibody in said animal, covalently bound to (2) one peptide selected from the group of peptides consisting of:

(a) a hydrophilic peptide, (b) a neutral peptide, (c) an amphipathic peptide, and (d) a second hybrid peptide comprising any combination of two or more of the above-defined peptides (a), (b) or (c), wherein each of said peptides (a), (b), (c) and (d) primes homologous helper T-cells and when administered by itself to an animal does not stimulate production of anti-peptide antibody in said animal, wherein, when said lipid is a phospholipid or spingolipid, said first hybrid peptide is covalently bound to a head group of said phospholipid or sphingolipid via a cross-linker, and wherein said immunogenic composition selectively induces antibody production in said animal to said peptides comprising said first hybrid peptide.

4. The essentially pure immunogenic composition of claim 3, further comprising at least two additional lipids, at least one of which is a sterol.

5. The essentially pure immunogenic composition of claim 3, wherein said first hybrid peptide comprises said hydrophilic peptide (2)(a) covalently bound to said amphipathic peptide (1).

6. The essentially pure immunogenic composition of claim 4, wherein said first hybrid peptide comprises said hydrophilic peptide (2)(a) covalently bound to said amphipathic peptide (1).

7. The essentially pure immunogenic composition of claim 1, wherein said lipid (A) is phosphatidylethanolamine.

8. The essentially pure immunogenic composition of claim 2, wherein said lipid (A) is phosphatidylethanolamine.

9. The essentially pure immunogenic composition of claim 3, wherein said lipid (A) is phosphatidylethanolamine.

10. The essentially pure immunogenic composition of claim 4, wherein said lipid (A) is phosphatidylethanolamine.

11. The essentially pure immunogenic composition of claim 2, wherein said lipid (A) is cholesterol.

12. The essentially pure immunogenic composition of claim 4, wherein said lipid (A) is cholesterol.

13. An essentially pure immunogenic composition comprising at least two immunogenic compositions selected from the group consisting of:

(I) an essentially pure immunogenic composition comprising:

(A) a lipid, which is one member selected from the group consisting of a phospholipid, sphingolipid, and sterol, each of which is a component of membranes of eukaryotic or prokaryotic cells, covalently bound to (B) an amphipathic peptide that primes homologous helper T-cells and that when administered by itself to an animal not stimulate production of anti-peptide antibody in said animal;

wherein, when said lipid (I)(A) is a phospholipid or sphingolipid, said amphipathic peptide is covalently bound to a head group of said phospholipid or sphingolipid via a cross-linker, and wherein said immunogenic composition (I) selectively induces antibody production in said animal to said amphipathic peptide;

(II) said essentially pure immunogenic composition (I), further comprising at least two additional lipids, at least one of which is a sterol;

(III) an essentially pure immunogenic composition comprising:
(A) a lipid, which is one member selected from the group consisting of a phospholipid, sphingolipid, and sterol, each of which is a component of membranes of eukaryotic or prokaryotic cells, covalently bound to
(B) a first hybrid peptide that is
(1) an amphipathic peptide that primes homologous helper T-cells and that when administered by itself to an animal does not stimulate production of anti-peptide antibody in said animal, covalently bound to
(2) one peptide selected from the group of peptides consisting of:
(a) a hydrophilic peptide,
(b) a neutral peptide,
(c) an amphipathic peptide, and
(d) a second hybrid peptide comprising combination of two or more of the above-defined peptides (a),(b) or (c), wherein each of said peptides (a), (b), (c) and (d) primes homologous helper T-cells and when administered by itself to an animal does not stimulate production of an anti-peptide antibody in said animal, wherein, when said lipid (III)(A) is a phospholipid or sphingolipid, said first hybrid peptide is covalently bound to head group of said phospholipid or sphingolipid via a cross-linker, and wherein said immunogenic composition (III) selectively induces antibody production in said animal to said peptides comprising said first hybrid peptide; and (IV) said essentially pure immunogenic composition (III), further comprising at least two additional lipids, at least one of which is a sterol.

14. An essentially pure immunogenic composition comprising at least two immunogenic compositions selected from the group consisting of:

(I) an essentially pure immunogenic composition comprising:
(A) a lipid, which is one member selected from the group consisting of a phosopholipid, sphingolipid, and sterol, each of which is a component of membranes of eukaryotic or prokaryotic cells, covalently bound to
(B) an amphipathic peptide that primes homologous helper T-cells and that when administered by itself to an animal not stimulate production of anti-peptide antibody in said animal;

wherein, when said lipid (I)(A) is a phospholipid or sphingolipid, said amphipathic peptide is covalently bound to ahead group of said phospholipid or sphingolipid via a cross-linker, and wherein said immunogenic composition (I) selectively induces antibody production in said animal to said amphipathic peptide, (II) said essentially pure immunogenic composition (I), further comprising at least two additional lipids, at least one of which is a sterol;

(III) an essentially pure immunogenic composition comprising;
(A) a lipid, which is one member selected from the group consisting of a phospholipid, sphingolipid, and sterol, each of which is a component of membranes of eukaryotic or prokaryotic cells, covalently bound to
(B) a first hybrid peptide that is
(1) an amphipathic peptide that primes homologous helper T-cell and that when administered by itself to an animal does not stimulate production of anti-peptide antibody in said animal, covalently bound to
(2) one peptide selected from the group of peptides consisting of;
(a) a hydrophilic peptide,
(b) a neutral peptide,
(c) an amphipathic peptide, and
(d) a second hybrid peptide comprising any combination of two or more of the above-defined peptides (a), (b) or (c), wherein each of said peptides (a), (b), (c) and (d) primes homologous helper T-cells and when administered by itself to an animal does not stimulate production of anti-peptide antibody in said animal, wherein, when said lipid (III)(A) is a phospholipid or sphingolipid, said first hybrid peptide is covalently bound to a head group of said phospholipid or sphingolipid via a cross-linker, and wherein said immunogenic composition (III) selectively induces antibody production in said animal to said peptides comprising said first hybrid peptide;

(IV) said essentially pure immunogenic composition (III), further comprising at least two additional lipids, at least one of which is a sterol; and (V) a composition comprising:
(A) said immunogenic composition (I) or (II), and
(B) a composition comprising:
(1) a lipid, which is one member selected from the group consisting of a phospholipid, sphingolipid, and sterol, each of which is a component of membranes of eukaryotic or prokaryotic cells, covalenty bound to
(2) at least one member selected from the group consisting of:
(a) a hydrophilic peptide that primes homologous helper T-cells and when administered by itself to an animal does not stimulate production of anti-peptide antibody in said animal,
(b) a neutral peptide that primes homologous helper T-cells and when administered by itself to an animal does not stimulate production of anti-peptide antibody in said animal,
(c) an amphipathic peptide that primes homologous helper T-cells and when administered by itself to an animal does not stimulate production of anti-peptide antibody in said animal, and
(d) a third hybrid peptide that is (i) an amphipathic peptide that primes homologous helper T-cells and when administered by itself to animal does not stimulate production of anti-peptide antibody in said animal, covalently bound to
(ii) one peptide selected from the group consisting of
(aa) a hydrophilic peptide,
(bb) a neutral peptide,
(cc) an amphipathic peptide, and
(dd) a fourth hybrid peptide comprising two or more of the said peptides (aa), (bb) or (cc),
wherein each of said peptides (aa), (bb), (cc) and (dd) primes homologous helper T-cells and when administered by itself to an animal does not stimulate production of anti-peptide antibody in said animal,
wherein, when said lipid (V)(B)(2)is a phospholipid or sphingolipid, said hydrophilic peptide (a), said neutral peptide (b), said amphipathic peptide (c) or said first hybrid peptide (d) is covalently to bound a head group of said phospholipid or sphingolipid via a cross-linker, and
(3) one or more lipids and one or more sterols.

15. The essentially pure immunogenic composition of claim 14, wherein said lipid (A) in said composition (I), (II), (III), (IV), or (V)(A) is phosphatidylethanolamine.

16. The essentially pure immunogenic composition of claim 14, wherein said lipid (A) in said composition (I), (II), (III), (IV), or (V)(A)is cholesterol.

17. The essentially pure immunogenic composition of claim 14, wherein said first hybrid peptide in said immunogenic composition (III) or (IV) comprises said hydrophilic peptide (2)(a) covalently bound to said amphipathic peptide (1).

18. The essentially pure immunogenic composition of claim 1, wherein said lipid (A) is a phospholipid.

19. The essentially pure immunogenic composition of claim 1, wherein said lipid (A) is a sphingolipid.

20. The essentially pure immunogenic composition of claim 1, wherein said lipid (A) is a sterol.

21. The essentially pure immunogenic composition of claim 3, wherein said lipid (A) is a phospholipid.

22. The essentially pure immunogenic composition of claim 3, wherein said lipid (A) is a sphingolipid.

23. The essentially pure immunogenic composition of claim 3, wherein said lipid (A) is a sterol.

24. The essentially pure immunogenic composition of claim 14, wherein said lipid (A) is a phospholipid.

25. The essentially pure immunogenic composition of claim 14, wherein said lipid (A) is a sphingolipid.

26. The essentially pure immunogenic composition of claim 14, wherein said lipid (A) is a sterol.

27. A pharmaceutical composition for selectively inducing antibody production, said composition comprising:
(A) the immunogenic composition of claim 1, and
(B) a pharmaceutically acceptable carrier, diluent or excipient.

28. A pharmaceutical composition for selectively inducing antibody production, said composition comprising:
(A) the immunogenic composition of claim 3, and
(B) a pharmaceutically acceptable carrier, diluent or excipient.

29. The pharmaceutical composition of claim 28, wherein said first hybrid peptide comprises said hydrophilic peptide (2)(a) covalently bound to said amphipathic peptide (1).

30. A pharmaceutical composition for selectively inducing antibody production, said composition comprising:
(A) the immunogenic composition of claim 14, and
(B) a pharmaceutically acceptable carrier, diluent or excipient.

31. The pharmaceutical composition of claim 30, wherein said first hybrid peptide in said immunogenic composition (III) or (IV) comprises said hydrophilic peptide (2)(a) covalently bound to said amphipathic peptide (1).

32. The pharmaceutical composition of claim 27, 28, or 30, wherein said lipid (A) is phosphatidylethanolamine.

33. The pharmaceutical composition of claim 27, 28, or 30, wherein said lipid (A) is cholesterol.

34. The pharmaceutical composition of claim 27, 28, or 30, wherein said lipid (A) is a phospholipid.

35. The pharmaceutical composition of claim 27, 28, or 30, wherein said lipid (A) is a sphingolipid.

36. The pharmaceutical composition of claim 27, 28, or 30, wherein said lipid (A) is a sterol.

37. A method for selectively inducing antibody production comprising administering to a host susceptible of treatment the immunogenic composition of claim 1, 18, 19, or 20.

38. A method for selectively inducing antibody production comprising administering to a host susceptible of treatment the immunogenic composition of claim 3, 21, 22, or 23.

39. The method of claim 38, wherein said first hybrid peptide comprises said hydrophilic peptide (2)(a) covalently bound to said amphipathic peptide (1).

40. A method for selectively inducing antibody production comprising administering to a host susceptible of treatment the immunogenic composition of claim 14, 24, 25, or 26.

41. The method of claim 40, wherein said first hybrid peptide in said immunogenic composition (III) or (IV) comprises said hydrophilic peptide (2)(a) covalently bound to said amphipathic peptide (1).

42. The method of claim 37, wherein said lipid (A) is phosphatidylethanolamine.

43. The method of claim 38, wherein said lipid (A) is phosphatidylethanolamine.

44. The method of claim 40, wherein said lipid (A) is phosphatidylethanolamine.

45. The method of claim 29, wherein said lipid (A) is cholesterol.

46. The method of claim 38, wherein said lipid (A) is cholesterol.

47. The method of claim 40, wherein said lipid (A) is cholesterol.

* * * * *